(12) United States Patent
Spataro et al.

(10) Patent No.: US 12,226,595 B2
(45) Date of Patent: Feb. 18, 2025

(54) INSTRUMENT DELIVERY DEVICE HAVING A ROTARY ELEMENT

(71) Applicant: Becton, Dickinson and Company, Franklin Lakes, NJ (US)

(72) Inventors: Joseph Spataro, Cottonwood Heights, UT (US); Jonathan Karl Burkholz, Salt Lake City, UT (US); S. Ray Isaacson, Layton, UT (US)

(73) Assignee: Becton, Dickinson and Company, Franklin Lakes, NJ (US)

( * ) Notice: Subject to any disclaimer, the term of this patent is extended or adjusted under 35 U.S.C. 154(b) by 1115 days.

(21) Appl. No.: 16/388,650

(22) Filed: Apr. 18, 2019

(65) Prior Publication Data

US 2019/0321595 A1    Oct. 24, 2019

Related U.S. Application Data

(60) Provisional application No. 62/660,661, filed on Apr. 20, 2018.

(51) Int. Cl.
*A61M 25/01* (2006.01)
*A61M 25/00* (2006.01)
(Continued)

(52) U.S. Cl.
CPC ...... *A61M 25/0113* (2013.01); *A61M 25/003* (2013.01); *A61M 25/0662* (2013.01);
(Continued)

(58) Field of Classification Search
CPC ...... A61M 25/0662; A61M 2025/0681; A61M 25/0113; A61M 25/0606;
(Continued)

(56) References Cited

U.S. PATENT DOCUMENTS

| 537,082 A | * | 4/1895 | Stuart | G01B 3/1069 33/762 |
| 2,711,734 A | * | 6/1955 | Moe | A61B 90/00 604/159 |

(Continued)

FOREIGN PATENT DOCUMENTS

| RU | 2763749 C2 * | 1/2022 | ......... A61B 5/15003 |
| WO | 03/084428 | 10/2003 | |
| WO | 2018/022402 | 2/2018 | |

*Primary Examiner* — Scott J Medway
(74) *Attorney, Agent, or Firm* — Kirton McConkie; Whitney Blair; Kevin Stinger (57) ABSTRACT

A delivery device for delivering an instrument through an intravenous catheter may include a housing, a rotary element disposed within the housing, and an instrument. In some embodiments, the rotary element may include a groove, which may extend around at least a portion of the circumference of the rotary element. In some embodiments, the instrument may be disposed within the groove and/or between the rotary element and the housing. In some embodiments, in response to rotation of the rotary element with respect to the housing, the instrument may be advanced distally through an outlet of the housing. In some embodiments, the instrument may include a guidewire, a probe, blood draw tubing, or a light tube.

15 Claims, 10 Drawing Sheets

(51) Int. Cl.
*A61M 25/06* (2006.01)
*A61M 25/09* (2006.01)

(52) U.S. Cl.
CPC .......... *A61M 25/09041* (2013.01); *A61M 2025/0031* (2013.01); *A61M 2025/0039* (2013.01); *A61M 25/0084* (2013.01); *A61M 2025/0177* (2013.01); *A61M 2025/0681* (2013.01); *A61M 2025/0687* (2013.01)

(58) Field of Classification Search
CPC ........... A61M 25/09041; A61M 39/08; A61M 25/002; A61M 39/00; A61M 2039/0276; A61B 17/3415; B65H 75/4471; B65H 2701/33; B65H 75/4402; B65H 75/4481; B65H 75/364
See application file for complete search history.

(56) References Cited

U.S. PATENT DOCUMENTS

| | | | |
|---|---|---|---|
| 3,545,608 A * | 12/1970 | Schnider et al. | A61B 17/06123 206/63.3 |
| 3,561,445 A * | 2/1971 | Katerndahl | A61M 25/0113 604/159 |
| 3,835,854 A * | 9/1974 | Jewett | A61M 25/0113 604/159 |
| 3,995,628 A * | 12/1976 | Gula | A61M 25/065 604/159 |
| 4,160,451 A * | 7/1979 | Chittenden | A61M 25/0113 242/405 |
| 4,342,313 A * | 8/1982 | Chittenden | A61M 25/0113 604/523 |
| 4,397,091 A * | 8/1983 | Gustavsson | A61M 25/0113 33/732 |
| 4,637,404 A * | 1/1987 | Gessman | A61N 1/056 607/126 |
| 4,713,059 A * | 12/1987 | Bickelhaupt | A61M 25/0113 242/588.6 |
| 4,850,974 A * | 7/1989 | Bickelhaupt | A61M 25/0113 604/171 |
| 4,860,757 A * | 8/1989 | Lynch | A61M 25/09041 600/585 |
| 5,098,391 A * | 3/1992 | Pantages | A61M 25/002 604/158 |
| 5,176,655 A * | 1/1993 | McCormick | A61M 25/0637 604/263 |
| 5,297,346 A * | 3/1994 | Weiner | A61B 1/00154 33/747 |
| 5,318,541 A * | 6/1994 | Viera | A61M 25/09041 604/159 |
| 5,344,011 A * | 9/1994 | DiBernardo | A61M 25/002 206/364 |
| 5,630,456 A * | 5/1997 | Hugo | E06B 9/326 242/395 |
| 5,810,835 A * | 9/1998 | Ryan | A61M 25/0113 606/108 |
| 5,827,202 A * | 10/1998 | Miraki | A61M 25/09041 604/95.01 |
| 5,843,002 A * | 12/1998 | Pecor | A61M 25/09041 604/528 |
| 5,855,567 A | 1/1999 | Reesemann | |
| 6,086,008 A * | 7/2000 | Gray | A61M 25/0113 604/528 |
| 6,093,179 A * | 7/2000 | O'Hara | A61J 15/0015 604/164.01 |
| 6,171,234 B1 * | 1/2001 | White | A61M 25/09041 600/102 |
| 6,231,564 B1 * | 5/2001 | Gambale | A61M 25/0113 604/528 |
| 6,327,507 B1 * | 12/2001 | Buchan | H02G 11/02 191/12.4 |
| 6,929,624 B1 * | 8/2005 | Del Castillo | A61M 25/0631 604/164.12 |
| 7,191,900 B2 * | 3/2007 | Opie | A61M 25/09 604/528 |
| 7,594,909 B2 * | 9/2009 | Mogensen | A61M 39/08 604/174 |
| 7,678,088 B2 * | 3/2010 | Egle | A61M 39/0208 604/288.01 |
| 8,029,481 B2 * | 10/2011 | Reavill | A61M 25/01 604/164.04 |
| 8,348,034 B2 * | 1/2013 | Fila | H02G 11/02 242/360 |
| 8,500,054 B2 * | 8/2013 | Grant | A61M 5/1418 242/346.1 |
| 8,651,412 B2 * | 2/2014 | Hernik | B65H 75/4481 242/588.3 |
| 8,702,025 B2 * | 4/2014 | Kish | A01K 27/004 242/378.1 |
| 8,728,035 B2 * | 5/2014 | Warring | A61M 25/0606 604/159 |
| 9,186,100 B2 | 11/2015 | Devgon | |
| 10,098,768 B2 * | 10/2018 | Cummins | A61F 2/95 |
| 10,118,018 B2 * | 11/2018 | Foley | A61M 25/0111 |
| 10,179,203 B1 * | 1/2019 | Huslage | A61M 39/08 |
| 10,265,499 B2 * | 4/2019 | Hong | A61M 27/00 |
| 10,617,846 B2 * | 4/2020 | Mitchell | A61M 25/0113 |
| 10,836,601 B2 * | 11/2020 | Akingba | A61M 25/09041 |
| 11,207,498 B2 * | 12/2021 | Devgon | A61M 25/0113 |
| 11,224,722 B2 * | 1/2022 | Moreno | A61M 25/09041 |
| 11,529,496 B2 * | 12/2022 | Yasunaga | A61M 25/0113 |
| 2002/0177814 A1 * | 11/2002 | Meng | A61M 39/045 604/164.07 |
| 2002/0195143 A1 * | 12/2002 | Paplow | B65H 75/4471 137/355.2 |
| 2004/0087966 A1 * | 5/2004 | McDevitt | A61M 25/09041 606/108 |
| 2005/0080476 A1 * | 4/2005 | Gunderson | A61F 2/95 623/1.11 |
| 2005/0197623 A1 * | 9/2005 | Leeflang | A61B 1/0055 604/95.04 |
| 2006/0015068 A1 * | 1/2006 | Amisar | A61M 25/0637 604/164.01 |
| 2007/0045460 A1 * | 3/2007 | Cupan | B65H 54/585 242/388.1 |
| 2007/0083184 A1 * | 4/2007 | Simpson | A61M 25/0113 604/500 |
| 2007/0203472 A1 | 8/2007 | Nachmani | |
| 2007/0250006 A1 * | 10/2007 | Court | A61B 90/11 604/117 |
| 2008/0319387 A1 | 12/2008 | Amisar et al. | |
| 2009/0071851 A1 * | 3/2009 | Maki | A61M 25/002 206/364 |
| 2009/0277988 A1 | 11/2009 | Hernik | |
| 2010/0094310 A1 | 4/2010 | Warring et al. | |
| 2010/0130923 A1 * | 5/2010 | Cleary | A61M 25/0113 606/41 |
| 2010/0174290 A1 * | 7/2010 | Wuebbeling | A61F 2/966 606/108 |
| 2012/0041537 A1 * | 2/2012 | Parker | A61F 2/95 623/1.11 |
| 2012/0277627 A1 * | 11/2012 | Devgon | A61B 5/150717 600/576 |
| 2012/0302952 A1 * | 11/2012 | Kitada | A61M 25/0043 604/525 |
| 2013/0060137 A1 * | 3/2013 | Uber, III | A61M 25/0113 600/435 |
| 2014/0299133 A1 | 10/2014 | Neely et al. | |
| 2015/0231313 A1 * | 8/2015 | O'Keefe | A61M 25/00 604/266 |
| 2015/0314104 A1 * | 11/2015 | Almansouri | A61M 25/0606 128/845 |
| 2016/0067470 A1 * | 3/2016 | Silva Pires e Albuquerque | A61M 39/0247 604/288.03 |
| 2016/0121086 A1 * | 5/2016 | Castro | A61M 25/0113 600/585 |

(56) References Cited

U.S. PATENT DOCUMENTS

| | | | |
|---|---|---|---|
| 2016/0136391 A1* | 5/2016 | Foley | A61M 25/0113 |
| | | | 604/544 |
| 2017/0128697 A1* | 5/2017 | Moisa | A61N 1/362 |
| 2017/0296792 A1* | 10/2017 | Ornelas Vargas | A61B 17/3468 |
| 2018/0021545 A1 | 1/2018 | Mitchell et al. | |
| 2018/0110968 A1* | 4/2018 | Ngo-Chu | A61M 29/02 |
| 2018/0353311 A1* | 12/2018 | Cummins | A61M 25/0136 |
| 2019/0143078 A1* | 5/2019 | Tierney | A61M 25/0133 |
| | | | 604/544 |
| 2020/0054863 A1* | 2/2020 | Boyle, Jr. | A61B 5/0823 |
| 2021/0236771 A1* | 8/2021 | Turner | A61M 25/0113 |

\* cited by examiner

INSTRUMENT DELIVERY DEVICE HAVING A ROTARY ELEMENT

RELATED APPLICATIONS

This application claims the benefit of U.S. Provisional Patent Application 62/660,661, filed Apr. 20, 2018, entitled INSTRUMENT DEVLIERY DEVICE HAVING A ROTARY ELEMENT, of which is incorporated herein in its entirety.

BACKGROUND

Insertion of a needle into vasculature of a patient tends to invoke apprehension in the patient, as well as the clinician, for various reasons. Blood draws are a common source of needle insertions. Attempts have been made to utilize peripheral intravenous catheters (PIVCs) for withdrawing blood from the vasculature of the patient, which may reduce may a number of needle insertions experienced by a given patient.

A common type of IV catheter is an over-the-needle PIVC. As its name implies, the over-the-needle PIVC may be mounted over an introducer needle having a sharp distal tip. The sharp distal tip may be used to pierce skin and the vasculature of the patient. Insertion of the PIVC into the vasculature may follow the piercing of the vasculature by the needle. The needle and the PIVC are generally inserted at a shallow angle through the skin into the vasculature of the patient with a bevel of the needle facing away from the skin of the patient. Once placement of the needle within the vasculature has been confirmed, the clinician may temporarily occlude flow in the vasculature and withdraw the needle, leaving the PIVC in place for future blood withdrawal and/or fluid infusion.

There may be several limitations to the current PIVC blood draw approach. Current use of a PIVC to draw blood can be slow and somewhat inefficient, particularly when the patient has difficult intra-venous access or veins that are not readily accessed by the clinician. Also, blood samples obtained via a PIVC may often need to be discarded due to concerns regarding sample quality. Furthermore, current use of a PIVC to draw blood may result in kinking of blood draw tubing. Moreover, the PIVC may narrow, collapse, or clog with time, leading to failure of the PIVC.

The subject matter claimed herein is not limited to embodiments that solve any disadvantages or that operate only in environments such as those described above. Rather, this background is only provided to illustrate one example technology area where some implementations described herein may be practiced.

SUMMARY

The present disclosure relates generally to a delivery device and related systems and methods for delivering an instrument through an intravenous catheter. In some embodiments, the instrument may include a guidewire, a probe, blood draw tubing, a light tube, or another suitable instrument. In some embodiments, the delivery device may include a housing, which may include an outlet. In some embodiments, the delivery device may include a rotary element, which may be disposed within the housing. In some embodiments, the rotary element may include a groove, which may extend around at least a portion of a circumference of the rotary element. In some embodiments, the delivery device may include the instrument, which may be disposed within the groove and/or between the rotary element and the housing. In some embodiments, in response to rotation of the rotary element with respect to the housing, the instrument may be advanced through the outlet.

In some embodiments, a catheter system may include a catheter assembly and the delivery device, which may be coupled to the catheter assembly. In some embodiments, the catheter assembly may include a catheter adapter and/or catheter tubing, which may extend distally from the catheter adapter. In some embodiments, in response to rotation of the rotary element with respect to the housing in a first direction, a distal end of the instrument may be disposed a first amount beyond a distal end of the catheter tubing. In some embodiments, in response to rotation of the rotary element with respect to the housing further in the first direction, the distal end of the instrument may be disposed a second amount beyond the distal end of the catheter tubing. In some embodiments, the second amount may be greater than the first amount.

In some embodiments, the groove may include a width approximately equal to or slightly greater than the instrument, which may facilitate support of the instrument and/or decrease a risk of kinking of the instrument. In some embodiments, the groove may extend inwardly from the circumference of the rotary element. In some embodiments, the groove may extend inwardly from the circumference of the rotary element to and/or towards a central axis of rotation of the rotary element. In some embodiments, a proximal end of the instrument may be secured within the delivery device.

In some embodiments, the instrument may include blood draw tubing, which may facilitate collection of blood from a patient. In some embodiments, the blood draw tubing may include a variable inner diameter and/or a variable outer diameter. In some embodiments, a proximal end of the blood draw tubing may be coupled to a blood collection device. In some embodiments, the delivery device may include additional tubing, which may extend from the top or the bottom of the rotary element. In some embodiments, the additional tubing may extend from the top or the bottom of the rotary element at the central axis of rotation of the rotary element. In some embodiments, the proximal end of the blood draw tubing may be coupled to the blood collection device via the additional tubing.

The object and advantages of the embodiments will be realized and achieved at least by the elements, features, and combinations particularly pointed out in the claims. It is to be understood that both the foregoing general description and the following detailed description are exemplary and explanatory and are not restrictive of the invention, as claimed.

BRIEF DESCRIPTION OF THE SEVERAL VIEWS OF THE DRAWINGS

Example embodiments will be described and explained with additional specificity and detail through the use of the accompanying drawings in which:

FIG. 2I is an upper perspective view of the catheter system of FIG. 2A coupled to a blood collection device, according to some embodiments;

DESCRIPTION OF EMBODIMENTS

Figure 1:
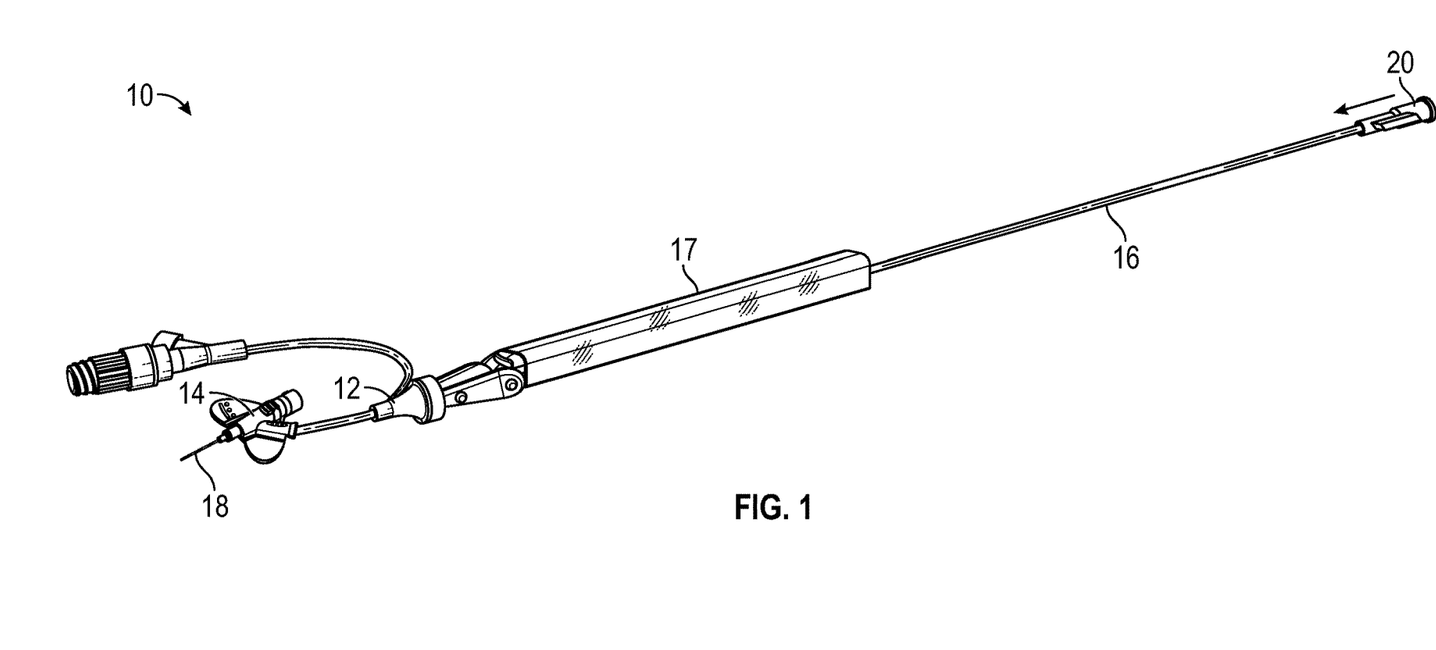
FIG. 1 is an upper perspective view of an example prior art catheter system, according to some embodiments.

Referring now to FIG. 1, a prior art blood draw device 10 is illustrated. The device 10 may attach to an extension set 12 of an indwelling peripheral intravenous catheter ("PIVC") 14, and tubing 16 of the device 10 may be pushed through the PIVC 14, which may extend an indwelling time of the PIVC 14. In further detail, the device 10 may allow a user to draw a blood sample from vasculature of a patient through the PIVC 14 when catheter tubing 18 of the PIVC 14 may no longer be functional due to, for example, debris build up on a tip of the catheter tubing 18 or collapse of the catheter tubing 18. Thus, the device 10 may reduce a number of needle sticks that the patient experiences.

The tubing 16 includes an extension tubing portion (illustrated in FIG. 1) and a blood draw tubing portion that is advanced beyond the catheter tubing 18 and is coupled to a distal end of the extension tubing portion. The tubing 16 may not be supported along a length of the device 10, which may lead to kinking of the blood draw tubing portion. Also, a connector 20, which may be configured to couple to a blood collection device, may move distally in response to advancement of the tubing 16 through the PIVC 14. In further detail, the connector 20 may move linearly or along an axis aligned with a longitudinal axis of the device 10 in response to advancement of the tubing 16 through the PIVC 14.

As used in the present disclosure, the term "distal" refers to a portion of a catheter system or component thereof that is farther from a user, and the term "proximal" refers to a portion of a catheter system or component thereof that is closer to the user. As used in the present disclosure, the term "user" may refer to a clinician, doctor, nurse, or any other care provider and may include support personnel.

Figure 2A:
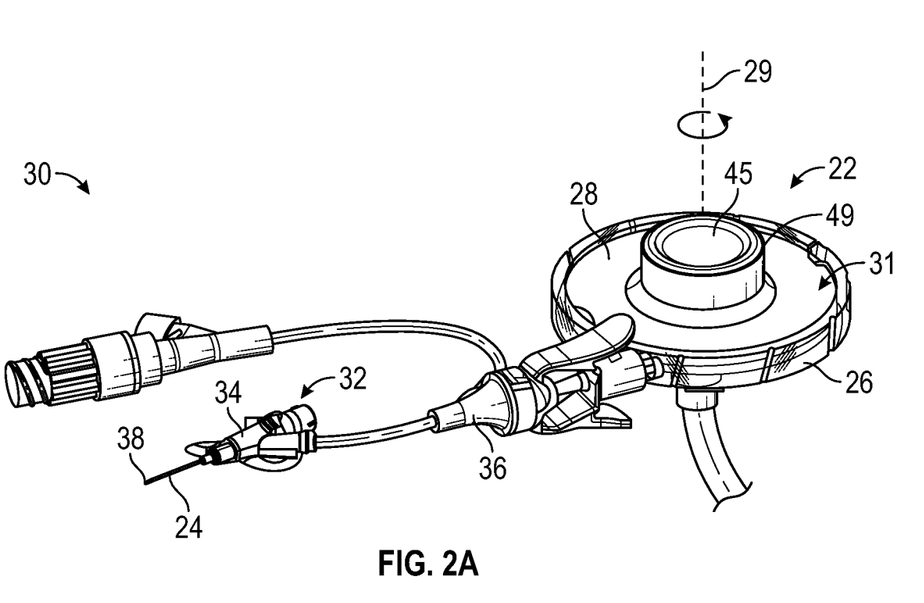
FIG. 2A is an upper perspective view of another catheter system, according to some embodiments.

Referring now to FIG. 2A, the present disclosure relates generally to a delivery device 22 for delivering an instrument through an intravenous catheter tubing 24 and related systems and methods. In some embodiments, the instrument may include a guidewire, a probe, blood draw tubing, a light tube, or another suitable instrument. In some embodiments, the delivery device 22 may facilitate advancement, through the catheter 24, of blood draw tubing that is softer than the prior art. In some embodiments, the blood draw tubing may be constructed of thermoplastic polyurethane (TPU), polyurethane, polyimide, nylon, TEFLON™, fluorinated ethylene propylene (FEP), or another suitable polymeric and/or elastomeric material. In some embodiments, the blood draw tubing may include a thinner wall and an inner diameter that provides faster blood collection full time than the prior art.

In some embodiments, the delivery device 22 may include a housing 26. In some embodiments, the delivery device 22 may include a rotary element 28, which may be disposed within the housing 26. In some embodiments, the housing 26 may include a generally cylindrical inner surface, which may allow a generally cylindrical outer surface of the rotary element 28 to rotate with respect to the housing 26. In some embodiments, the housing 26 may include an inner surface that is another shape other than generally cylindrical, and an outer surface of the rotary element 28 may include a shape corresponding to the other shape that allows the rotary element 28 to rotate with respect to the housing 26.

In some embodiments, in response to rotation of the rotary element 28 with respect to the housing 26, the instrument may be distally advanced. In some embodiments, the rotary element 28 may revolve around a central axis of rotation 29. In some embodiments, the housing 26 may include an upper and/or lower rim or ledge which may prevent the rotary element 28 from exiting an upper opening 31 and/or lower opening 33 (illustrated in FIG. 2H) of the housing 26.

FIG. 2A illustrates a catheter system 30, according to some embodiments. In some embodiments, the catheter system 30 may include a catheter assembly 32 and the delivery device 22, which may be coupled to the catheter assembly 32. In some embodiments, the catheter assembly 32 may include a catheter adapter 34 and the catheter tubing 24, which may extend distally from the catheter adapter 34. In some embodiments, the catheter tubing 24 may be secured within the catheter adapter 34. In some embodiments, the catheter assembly 32 may include a PIVC.

In some embodiments, the delivery device 22 may be directly coupled to a proximal end of the catheter adapter 34. In these and other embodiments, the catheter assembly 32 may include a straight or non-integrated catheter assembly. In some embodiments, the delivery device 22 may be coupled to an extension set 36 of the catheter assembly 32, as illustrated in FIG. 2A. In these and other embodiments, the catheter assembly 32 may include an integrated catheter assembly. In further detail, in some embodiments, the catheter adapter 34 of the catheter assembly 32 may include an integrated extension tube, such as, for example, the BD NEXIVA™ Closed IV Catheter System, the BD NEXIVA™ DIFFUSICS™ Closed IV Catheter System, or the Becton Dickinson PEGASUS™ Safety Closed IV Catheter System.

Figure 2B:
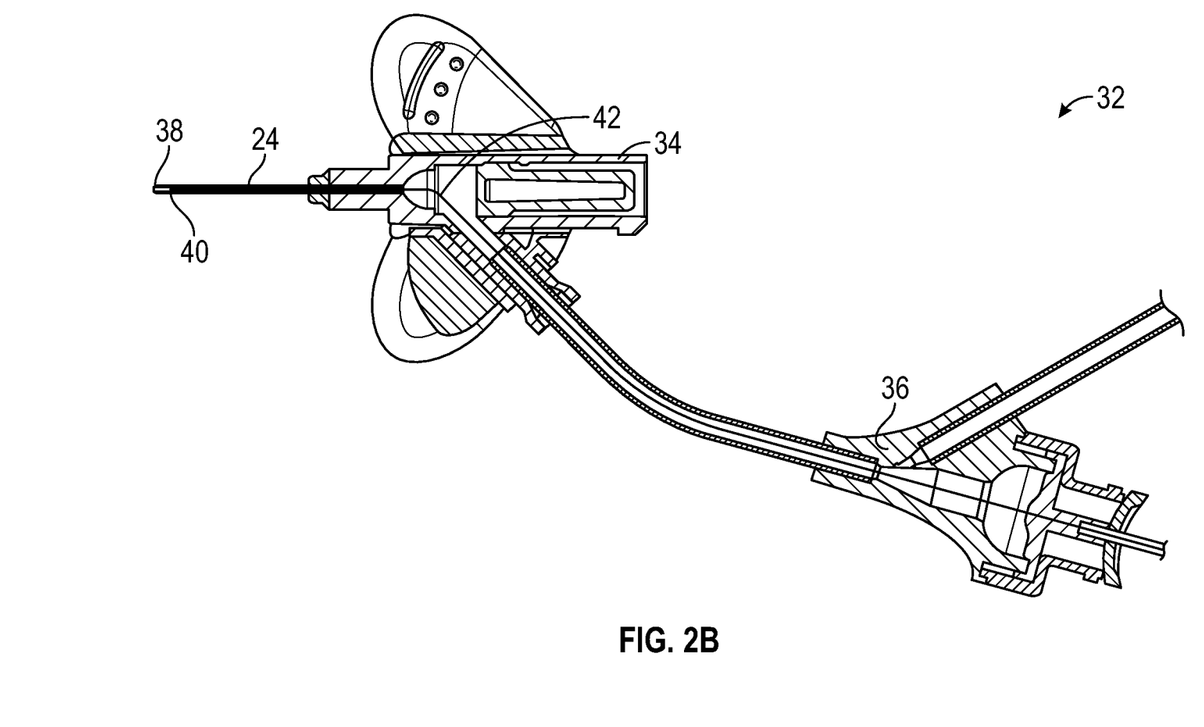
FIG. 2B is a cross-sectional view of an example catheter assembly of the catheter system of FIG. 2A, illustrating an example instrument in a retracted or proximal position, according to some embodiments.
Figure 2C:
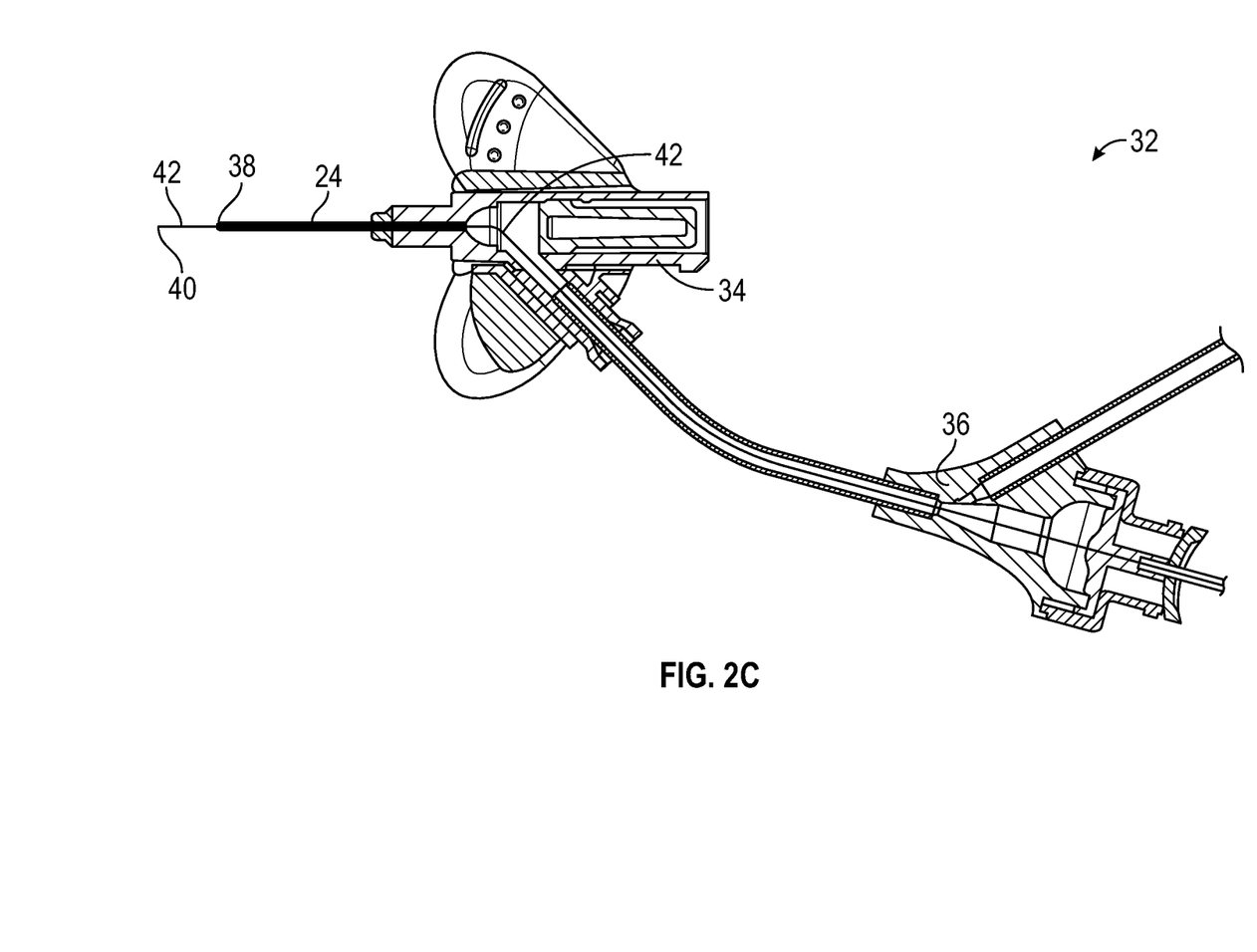
FIG. 2C is a cross-sectional view of the catheter assembly of the catheter system of FIG. 2A, illustrating the instrument in an advanced or distal position, according to some embodiments.

In some embodiments, in response to rotation of the rotary element 28 with respect to the housing 26 in a first direction, a distal end of the instrument may be advanced beyond a distal end 38 of the catheter tubing 24. Referring now to FIGS. 2B-2C, in some embodiments, in response to rotation of the rotary element 28 with respect to the housing 26 in the first direction, the distal end 40 of the instrument 42 may be disposed at a first location with respect to the catheter assembly 32. An example first location is illustrated in FIG. 2B. In some embodiments, in response to rotation of the rotary element 28 with respect to the housing further in the first direction, the distal end 40 of the instrument 42 may be disposed at a second location with respect to the catheter assembly 32. In some embodiments, the second location may be distal to the first location. An example second location is illustrated in FIG. 2C. In some embodiments, the instrument 42 may be continuously advanced in the distal direction as the rotary element 28 is continuously turned.

In some embodiments, in response to rotation of the rotary element 28 with respect to the housing 26 in the first direction, the distal end 40 of the instrument 42 may be disposed a first amount beyond the distal end 34 of the catheter tubing 24. In some embodiments, in response to rotation of the rotary element 28 with respect to the housing 26 further in the first direction, the distal end 40 of the instrument 42 may be disposed a second amount beyond the distal end 34 of the catheter tubing 24. In some embodiments, the second amount may be greater than the first amount.

In some embodiments, the rotary element 28 may also rotate with respect to the housing 26 in a second direction opposite to the first direction. In some embodiments, in response to rotation of the rotary element 28 with respect to the housing 26 in the second direction, the distal end 40 of the instrument 42 may be moved proximally. In some embodiments, in response to rotation of the rotary element 28 with respect to the housing 26 in the second direction, the distal end 40 of the instrument 42 may be partially or fully retracted.

Figure 2D:
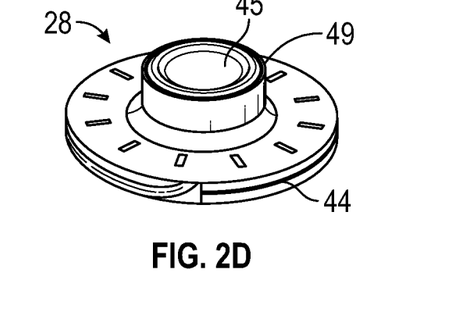
FIG. 2D is an upper perspective view of an example rotary element of the catheter system of FIG. 2A, according to some embodiments.

Referring now to FIG. 2D, in some embodiments, the rotary element 28 may include a support surface or groove 44, which may extend around at least a portion of a circumference of the rotary element 28. In some embodiments, the groove 44 may include a width approximately equal to or slightly greater than the instrument 42, which may facilitate support of the instrument 42 and/or decrease a risk of kinking of the instrument 42. In some embodiments, a length of the groove 44 may extend inwardly from the circumference of the rotary element, as illustrated in FIG. 2D, which may facilitate support of the instrument 42 as the instrument 42 exits the rotary element 28. In some embodiments, a top surface of the rotary element 28 may include a protrusion 45.

In some embodiments, the delivery device 22 may include a torque limiter, which may limit a torque of a user interface 49. In some embodiments, the torque limiter may limit the torque by slipping (as in, e.g., a friction plate slip-clutch, magnetic particle, or magnetic hysteresis torque limiter) or by uncoupling the load entirely (as in, e.g., a shear pin, synchronous magnetic, ball detent, or pawl and spring torque limiter). In further detail, in some embodiments, the user interface 49 may be coupled to and rotate with the rotary element 28 in response to the torque below a predetermined, threshold value. In some embodiments, the user may grip and turn the user interface 49 to advance and/or retract the instrument 42. In some embodiments, in response to the torque of the user interface 49 exceeding the threshold value, the user interface 49 may release from the rotary element 28 or slip with respect to the rotary element 28, which may prevent the instrument 42 from causing vascular damage, kinking, and/or buckling. In some embodiments, when the user interface 49 releases from the rotary element 28 or slips with respect to the rotary element 28, the user may not be able to rotate the rotary element 28 via the user interface 49. In some embodiments, the rotary element 28 may not include the torque limiter and/or the user interface 49. In these and other embodiments, the protrusion 45 may act as a grip.

In some embodiments, rotation of the rotary element 28 with respect to the housing 26 may be accomplished via direct user input in which the user may physically interact with or touch the rotary element 28. For example, a hand of the user may take hold of the protrusion 45 and/or the user interface 49 to rotate the rotary element 28. In other embodiments, the rotation of the rotary element 28 with respect to the housing 26 may be driven through a mechanical coupling. In these and other embodiments, the user may not physically interact with or touch the rotary element 28 and/or the rotation of the rotary element 28 may occur in response to a linear or non-rotating action from the user, which may be introduced via a geared coupling to the rotary element 28. In some embodiments, the device may translate the linear or non-rotating action of the user into rotation of the rotary element 28.

Figure 2E:
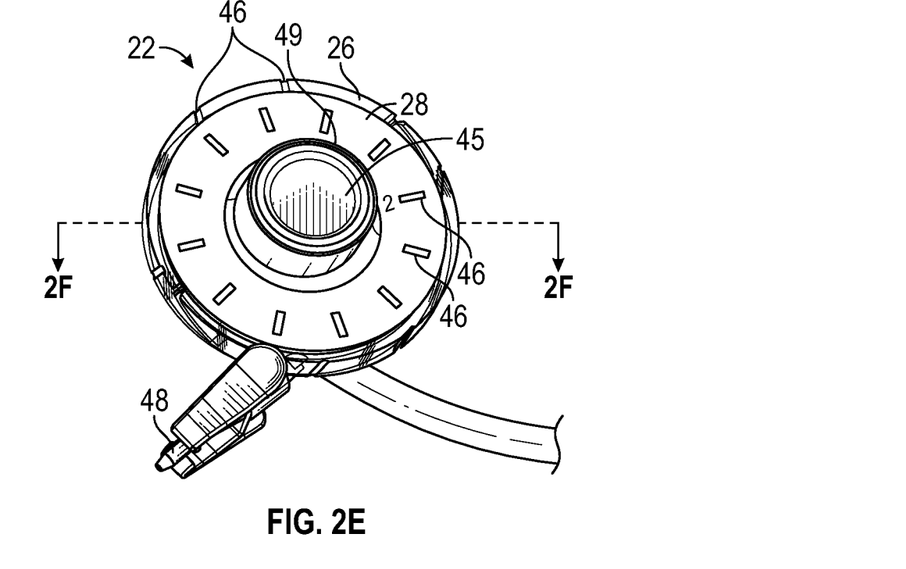
FIG. 2E is an upper perspective view of an example delivery device of the catheter system of FIG. 2A, according to some embodiments.

Referring now to FIG. 2E, the rotary element 28 is illustrated disposed within the housing 26, according to some embodiments. In some embodiments, the rotary element 28 and/or the housing 26 may include one or more markings 46, which may be visible to the user. In some embodiments, the markings 46 may correspond to an insertion distance of the instrument 42. In some embodiments, the distal end 40 of the instrument 42 may be disposed in a particular location with respect to the catheter assembly 32 in response to the user turning the rotary element 28 to align a particular marking 46 of the housing with a particular marking 46 of the rotary element 28. In some embodiments, at least some of the markings 46 may include detents, which may be configured to hold the rotary element 28 at predetermined positions and/or provide resistance to movement of the rotary element 28 from the detents.

Figure 2F:
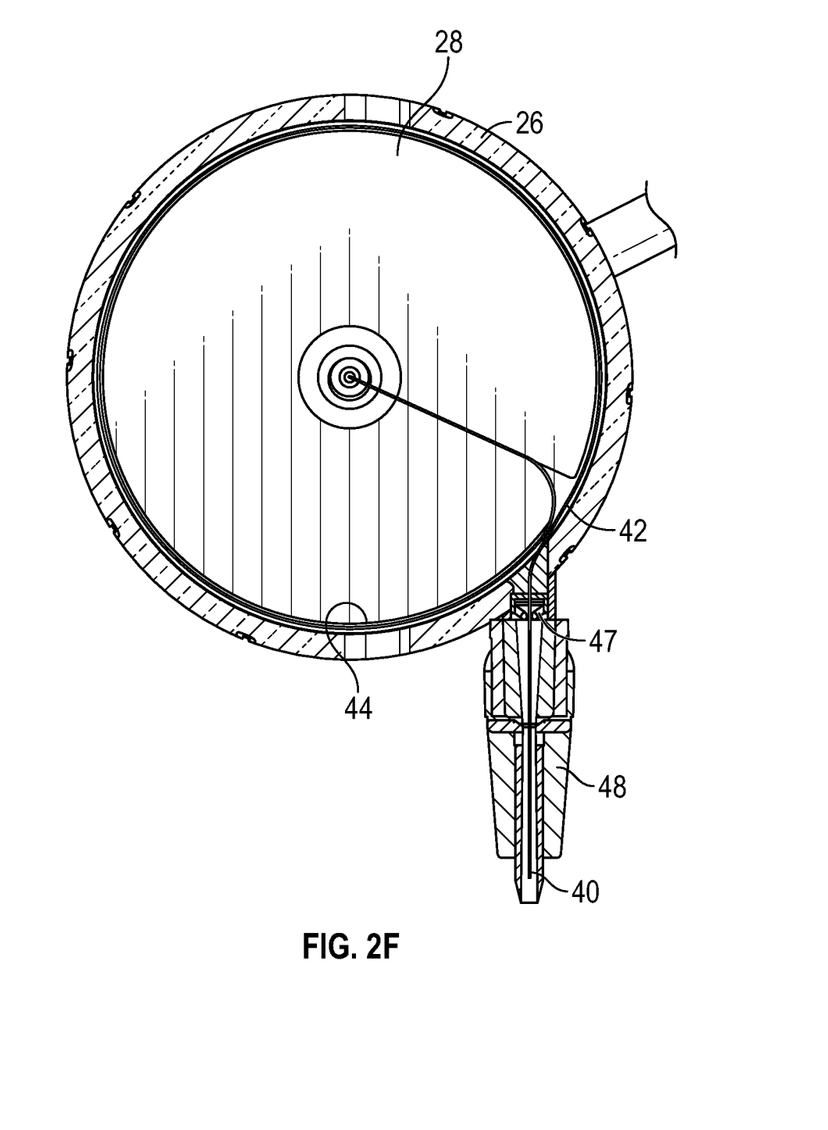
FIG. 2F is a cross-sectional view of the delivery device of FIG. 2E along the line 2F-2F, according to some embodiments.

Referring now to FIG. 2F, a cross-section through the groove 44 is illustrated, according to some embodiments. In some embodiments, the instrument 42 may be disposed within the groove 44 and/or between the rotary element 28 and the housing 26. In some embodiments, in response to rotation of the rotary element 28 with respect to the housing 26, the instrument 42 may be advanced through an outlet of the housing 26. In some embodiments, the outlet of the housing 26 may include a port 48. In some embodiments, the port 48 may include a male or female luer.

In some embodiments, the port 48 may include an elastomeric seal or septum 47. In some embodiments, the septum 47 may be disposed in the housing 26 between the rotary element 28 and the port 48. In some embodiments, the septum 47 may maintain a seal when the instrument 42 is moved through the septum 47 and/or disposed within the septum 47, which may prevent fluid from leaking into the housing 26 and/or rotary element 28. In some embodiments, in addition to or as an alternative to the septum 47, an adhesive and/or potting agent may be disposed in the housing 26 between the rotary element 28 and the port 48. In some embodiments, the septum 47 may be assembled onto the instrument 42 and then sandwiched during assembly between the rotary element 28 and the port 48 to create a seal around the instrument 42. In some embodiments, the septum 47 may include a slit. In some embodiments, during assembly, the septum 47 may be secured within the housing 26 during assembly and/or the instrument 42 may then be inserted through the septum 47, which may be compliant.

In some embodiments, an extension tube (not illustrated) may be coupled to the port 48 and/or may extend between the port 48 and the extension set 36. In some embodiments, the extension tube may be flexible to introduce additional degrees of freedom within the catheter system 30. In some embodiments, a proximal end of the extension tube may be integrated with the port 48 or coupled to the port 48 via a connector. In some embodiments, a distal end of the extension tube may include another connector. In some embodiments, the distal end of the extension tube may be integrated with the extension set 36 or another element or coupled to the extension set 36 via the another connector.

In some embodiments, a length of the groove 44 may extend inwardly from the circumference of the rotary element 28 to and/or towards the central axis of rotation 29 of the rotary element 28. In some embodiments, at a location at which the groove 44 extends inwardly from the circumference of the rotary element 28, the groove 44 may include a gradual curve, which may avoid kinking of the instrument 42.

In some embodiments, the length of the groove 44 may extend inwardly from the circumference of the rotary element to the central axis of rotation 29, which may facilitate support of the instrument 42 as the instrument 42 exits the rotary element 28. In some embodiments, the instrument 42 may exit the rotary element 28 at another location other than the central axis of rotation 29, and the groove 44 may extend to the other location. In some embodiments, the instrument may not exit the rotary element 28 and/or a proximal end of the instrument may be secured to the rotary element 28, as will be discussed in further detail with respect to FIG. 3. In some embodiments, a portion of the groove 44 disposed inwardly from the circumference may be part of a slit or tunnel.

Figure 2G:
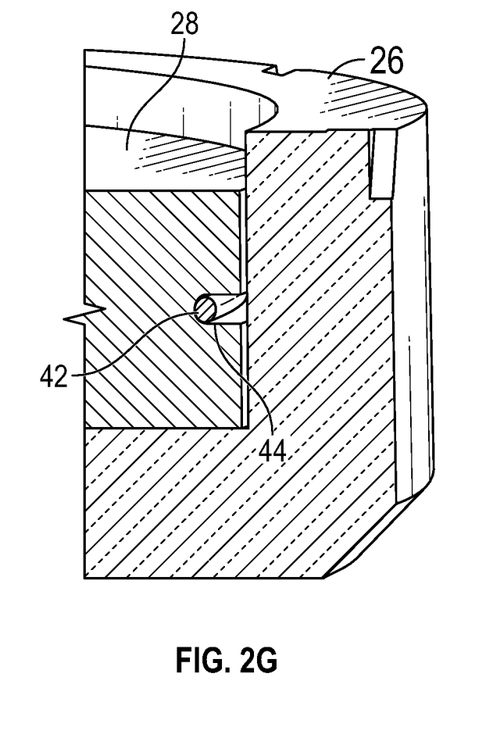
FIG. 2G is an enlarged partial cross-sectional view of the delivery device of FIG. 2E, according to some embodiments.

Referring now to FIG. 2G, in some embodiments, the instrument 42 may be disposed within the groove 44 and supported on both sides of the instrument 42. In some embodiments, the housing 26 may block the groove 44 to prevent the instrument 42 from laterally exiting the groove 44. As illustrated in FIG. 2G, in some embodiments, the groove 44 may include a width approximately equal to or slightly greater than the instrument 42, which may facilitate support of the instrument 42 and/or decrease a risk of kinking of the instrument 42.

Referring to FIG. 2A, in some embodiments, the instrument 42 may include a probe, sensor, light pipe, guidewire, or blood draw tubing. In some embodiments, the probe may include a light-emitting disinfection probe. In some embodiments, the instrument 42 may be coupled with a power source through a rotationally allowable contact. In some embodiments, the housing 26 and/or the rotary element 28 may include a battery and/or power switch.

In some embodiments, the instrument 42 may include blood draw tubing, which may have properties and geometries that vary along the length of the blood draw tubing. In some embodiments, the properties and geometries of the blood draw tubing my vary to locally improve stiffness or compliance of the tubing, reduce a time to fill the blood collection device with blood, reduce a risk of sample degradation (hemolysis, etc.), or reduce vein trauma and associated downstream trauma.

Figure 2H:
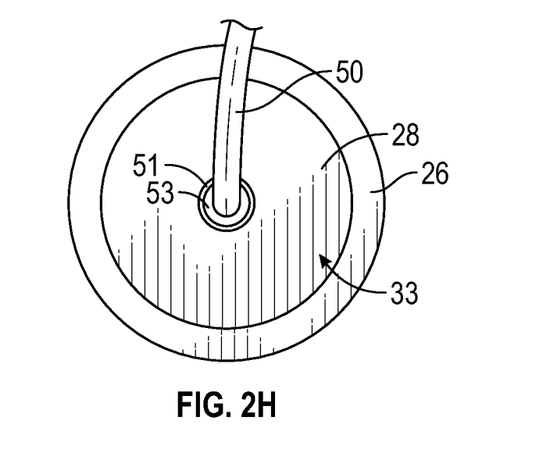
FIG. 2H is a bottom view of the delivery device of FIG. 2E, according to some embodiments.

Referring now to FIG. 2H, in some embodiments, the delivery device may include tubing 50. In some embodiments, the tubing 50 may be coupled to a top or bottom of the rotary element 28 via a connector 51. In some embodiments, the connector 51 may include a luer adapter, such as a male or female luer adapter, or another suitable connector 51. In some embodiments, the connector 51 may be integral with the top or bottom of the rotary element 28. In some embodiments, the connector 51 may be coupled to the top or bottom of the rotary element 28 to allow the connector 51 to rotate independently of the rotary element 28. In these and other embodiments, the connector 51 and the tubing 50, as well as any devices coupled to an end of the tubing opposite the connector 51, may remain stationary in response to rotation of the rotary element 28. In some embodiments, the tubing 50 may include a corresponding connector 53, which may couple to the connector 51 to secure the tubing 50 to the connector 51.

In some embodiments, the tubing 50 may extend from the top or the bottom of the rotary element 28 or from the connector 51 at the central axis of rotation 29 of the rotary element 28. In some embodiments, the tubing 50 may extend from the top or bottom of the rotary element 28 or from the connector 51 at a location other than the central axis of rotation 29. In some embodiments, a proximal end of the instrument 42 may be coupled to and/or extend through the tubing 50. In some embodiments, the rotary element 29 may not include the tubing 50 and/or an opening allowing access to the tubing 50. In some embodiments, the tubing 50 may be protective of one or more wires or other parts of the instrument 42.

Referring now to FIG. 2I, in some embodiments, the instrument 42 may include catheter or blood draw tubing, and a proximal end of the instrument 42 may be coupled to a blood collection device 52 via the tubing 50. In some embodiments, the blood collection device 52 may be disposed within a connector 54 disposed at an end of the tubing 50. In some embodiments, the tubing 50 may include a larger inner diameter than the blood draw tubing, which may facilitate speedy collection of blood. In some embodiments, the blood collection device 52 may include any suitable type of blood collection device. For example, the blood collection device 52 may include a syringe. In some embodiments, the blood draw tubing may include a variable inner diameter and/or a variable outer diameter.

In some embodiments, the connector 54 and/or the blood collection device 52 may not move linearly or along the axis aligned with the longitudinal axis of the catheter assembly 32 in response to advancement of the blood draw tubing through the catheter assembly 32. In some embodiments, the blood collection device 52 may rotate, but may not move with respect to the longitudinal axis of the catheter assembly 32.

Figure 3:
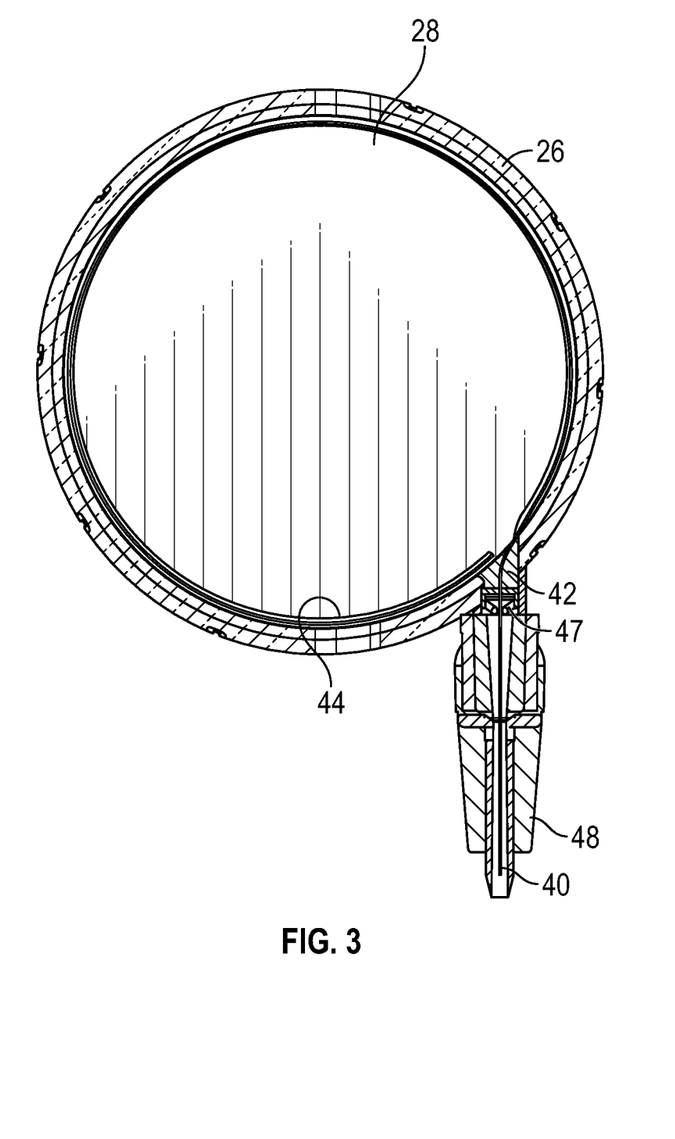
FIG. 3 is an alternative cross-sectional view of the delivery device of FIG. 2E without example tubing, according to some embodiments.

In some embodiments, a first or distal end of the instrument 42 may be moveable, while a second or proximal end of the instrument 42 may be secured. For example, the proximal end of the instrument 42 may be secured within the delivery device 22. Referring now to FIG. 3, in some embodiments, the proximal end of the instrument 42 may be disposed within the groove 44 and/or at the circumference of the rotary element 28. In these and other embodiments, the instrument 42 may include a guidewire to facilitate placement of the catheter tubing 24 in the patient, who may have difficult and/or fragile venous access. In these and other embodiments, the rotary element 28 may not include the tubing 50. In some embodiments, the lower opening of the housing 26 may be closed.

Figure 2J:
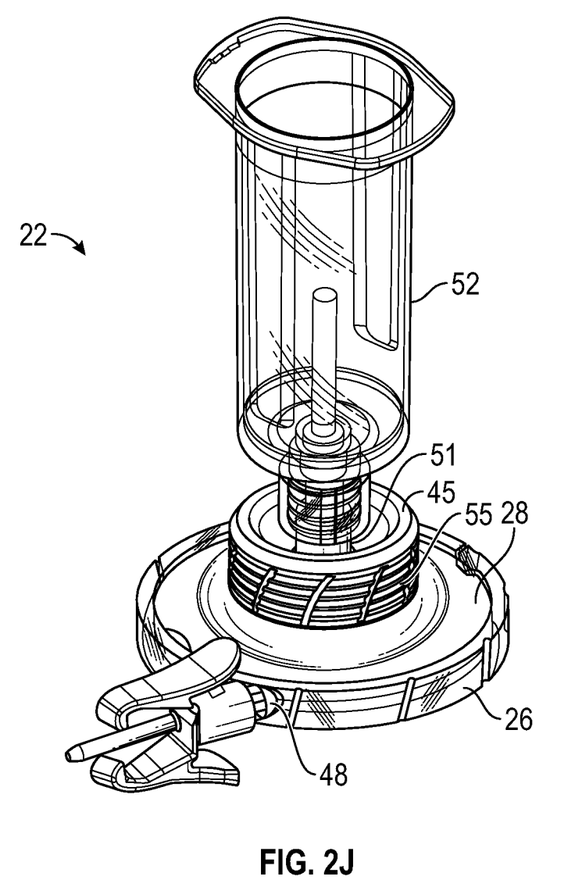
FIG. 2J is an upper perspective view of the delivery device of FIG. 2E, according to some embodiments.

Referring now to FIG. 2J, in some embodiments, the catheter system delivery device 22 may not include the tubing 50. In some embodiments, the blood collection device 52 may be coupled directly to the connector 51. In some embodiments, the blood collection device 52 may include a syringe, a vacuum tube, a blood collection tube, a holder, etc. In some embodiments, the holder may include a cannula configured to puncture a seal of a particular blood collection device. In some embodiments, the top and/or the bottom of the rotary element 28 may include a connector 51. In some embodiments, the blood collection device may be integrated with the connector 51 or monolithically formed with the connector 51 as a single unit.

In some embodiments, the delivery device 22 may include an automated passive feature that allows the rotary element 28 to rotate in response to coupling of blood collection device 52 to the connector 51. Thus, in some embodiments, the instrument 42 may be prevented from prematurely exiting the delivery device 22. In some embodiments, the delivery device 22 may include an manual user input feature, such as, for example, a lever or a button, that allows the rotary element 28 to rotate or prevents the rotary element 28 from rotating.

In some embodiments, the user may grip and turn the user interface 55 to advance and/or retract the instrument 42. In some embodiments, in response to the torque of the user interface 55 exceeding the threshold value, the user interface 55 may release from the rotary element 28 or slip with respect to the rotary element 28, which may prevent the instrument 42 from causing vascular damage, kinking, and/or buckling. In some embodiments, when the user interface 55 releases from the rotary element 28 or slips with respect to the rotary element 28, the user may not be able to rotate the rotary element 28 via the user interface 55. In some embodiments, the rotary element 28 may not include the torque limiter and/or the user interface 55. In these and other embodiments, the protrusion 45 may act as a grip for the user.

All examples and conditional language recited herein are intended for pedagogical objects to aid the reader in understanding the invention and the concepts contributed by the inventor to furthering the art, and are to be construed as being without limitation to such specifically recited examples and conditions. Although embodiments of the present inventions have been described in detail, it should be understood that the various changes, substitutions, and alterations could be made hereto without departing from the spirit and scope of the invention.

The invention claimed is:

1. A delivery device for delivering an instrument through an intravenous catheter, comprising:
    a housing having an outlet;
    a rotary element disposed within the housing, the rotary element having a groove, the rotary element further comprising a cylindrical protrusion aligned with a central axis of the rotary element, the rotary element further comprising a top surface extending outwardly from the cylindrical protrusion towards the housing, wherein an entirety of an outer surface of the cylindrical protrusion is exposed such that the cylindrical protrusion is configured to be gripped by a user to rotate the rotary element around the central axis of rotation of the rotary element;
    an instrument disposed within the groove and between the rotary element and the housing to prevent the instrument from laterally exiting the groove in a direction away from the central axis of the rotary element, wherein the instrument extends around at least a portion of a circumference of the rotary element within the groove, wherein in response to rotation of the rotary element with respect to the housing, the instrument is advanced distally through the outlet;
    a first connector coupled to the rotary element;
    a second connector configured to couple to a blood collection device; and
    additional tubing comprising a first end coupled to the first connector and a second end coupled to the second connector, wherein the additional tubing extends from the first connector at a central axis of rotation of the rotary element.

2. The delivery device of claim 1, wherein the instrument comprises a guidewire.

3. The delivery device of claim 2, wherein a proximal end of the guidewire is secured within the delivery device.

4. The delivery device of claim 1, wherein the instrument comprises a probe.

5. The delivery device of claim 1, wherein the instrument comprises another tubing.

6. The delivery device of claim 1, wherein the groove extends inwardly from the circumference toward a central axis of rotation of the rotary element.

7. A method, comprising:
    coupling a delivery device to a connector of a catheter assembly, wherein the catheter assembly comprises a catheter adapter having a side port, wherein the catheter assembly further comprises an extension tube having a distal end coupled to the side port and a proximal end coupled to the connector, wherein the delivery device comprises a housing having an outlet, a rotary element disposed within the housing, and an instrument;
    rotating the rotary element with respect to the housing in a first direction, wherein the rotary element is disposed within the housing, wherein the rotary element comprises a groove, wherein the instrument extends around at least a portion of a circumference of the rotary element within the groove, wherein the instrument is disposed within the groove and between the rotary element and the housing to prevent the instrument from laterally exiting the groove in a direction away from a central axis of the rotary element, wherein in response to rotating the rotary element with respect to the housing in the first direction, a distal end of an instrument is advanced through the extension tube and side port and beyond a distal end of a catheter, wherein the rotary element comprises a cylindrical protrusion aligned with the central axis of rotation of the rotary element configured to be gripped by a user to rotate the rotary element around the central axis of rotation of the rotary element, wherein rotating the rotary element with respect to the housing in a first direction comprises gripping the cylindrical protrusion to turn the rotary element with respect to the housing, the rotary element further comprising a top surface extending outwardly from the cylindrical protrusion towards the housing, wherein an entirety of an outer surface of the cylindrical protrusion is exposed such that the cylindrical protrusion is configured to be gripped by a user to rotate the rotary element around the central axis of rotation of the rotary element.

8. The method of claim 7, wherein the instrument comprises blood draw tubing.

9. The method of claim 7, further comprising rotating the rotary element with respect to the housing in a second direction opposite the first direction, wherein in response to rotating the rotary element with respect to the housing in a second direction opposite the first direction, the distal end of the instrument is retracted.

10. A delivery device for delivering an instrument through an intravenous catheter, comprising:
    a housing;
    a port extending outwardly from the housing, wherein the port comprises a male luer;
    a rotary element disposed within the housing, the rotary element having a groove, wherein the rotary element comprises a cylindrical protrusion aligned with a central axis of rotation of the rotary element configured to be gripped by a user to rotate the rotary element around the central axis of rotation of the rotary element, the rotary element further comprising a top surface extending outwardly from the cylindrical protrusion towards the housing, wherein the top surface comprises a plurality of markings each corresponding to an insertion distance of an instrument; and the instrument disposed within the groove and between the rotary element and the housing to prevent the instrument from laterally exiting the groove in a direction away from the central axis of the rotary element, wherein the instrument extends around at least a portion of a circumference of the rotary element within the groove, wherein in response to rotation of the rotary element with respect to the housing, the instrument is advanced distally through the port.

11. The delivery device of claim 10, wherein the instrument comprises a guidewire.

12. The catheter system of claim 11, wherein a proximal end of the guidewire is secured within the delivery device.

13. The delivery device of claim 10, wherein the instrument comprises a probe.

14. The delivery device of claim 10, wherein the instrument comprises tubing.

15. The delivery device of claim 10, wherein the groove extends inwardly from the circumference toward the central axis of rotation of the rotary element.

* * * * *